US011154456B2

(12) United States Patent
Caetano (10) Patent No.: US 11,154,456 B2
(45) Date of Patent: Oct. 26, 2021

(54) VALVE WITH ON-OFF MECHANISM FOR BAG USED FOR CONDITIONING, RECONSTITUTING AND/OR DILUTING OF INJECTABLE PRODUCTS

(71) Applicant: Norival Caetano, Sao Paulo (BR)

(72) Inventor: Norival Caetano, Sao Paulo (BR)

( * ) Notice: Subject to any disclaimer, the term of this patent is extended or adjusted under 35 U.S.C. 154(b) by 469 days.

(21) Appl. No.: 16/317,467

(22) PCT Filed: Jul. 6, 2017

(86) PCT No.: PCT/BR2017/050183
§ 371 (c)(1),
(2) Date: Jan. 11, 2019

(87) PCT Pub. No.: WO2018/009996
PCT Pub. Date: Jan. 18, 2018

(65) Prior Publication Data
US 2019/0298608 A1    Oct. 3, 2019

(30) Foreign Application Priority Data

Jul. 11, 2016 (BR) .................. BR 10 20160160910

(51) Int. Cl.
*A61J 1/10* (2006.01)
*A61M 39/22* (2006.01)
*A61J 1/20* (2006.01)

(52) U.S. Cl.
CPC .............. *A61J 1/10* (2013.01); *A61M 39/22* (2013.01); *A61J 1/20* (2013.01)

(58) Field of Classification Search
CPC ......... A61M 39/26; A61M 39/22; A61J 1/10; A61J 1/20; A61J 1/1475
See application file for complete search history.

(56) References Cited

U.S. PATENT DOCUMENTS

| 4,146,153 | A | 3/1979 | Bailen | |
| 5,762,646 | A * | 6/1998 | Cotter | A61J 1/1487 |
| | | | | 604/410 |
| 9,933,094 | B2 * | 4/2018 | Fangrow | A61M 39/26 |
| 2016/0305574 | A1 * | 10/2016 | Burdge | A61M 39/18 |
| 2017/0027820 | A1 | 2/2017 | Okiyama et al. | |

FOREIGN PATENT DOCUMENTS

| BR | PI 1003460-9 | 1/2013 |
| WO | 2012040799 A1 | 4/2012 |

OTHER PUBLICATIONS

International Search Report dated Sep. 15, 2017, issued in International Application No. PCT/BR2017/050183 (4 pages).

* cited by examiner

*Primary Examiner* — Ariana Zimbouski
(74) *Attorney, Agent, or Firm* — Patshegen IP LLC; Moshe Pinchas (57) ABSTRACT

A valve with an on-off mechanism for a bag used for conditioning, reconstituting, and/or diluting of injectable products, with the valve integrated to the single access point of a bag; the valve includes an open-close mechanism that enables a syringe or an infusion equipment, both including a luer-lock terminal, to be directly coupled to said valve; the valve comprises five basic components: the tapered base, the mobile tapered part, a smaller diameter sealing O-ring, a larger diameter sealing O-ring, and the cover that protects the terminal with a luer-lock type thread; the valve removes the requirement of using metallic needles or plastic spikes during practical use of the bag.

20 Claims, 15 Drawing Sheets

VALVE WITH ON-OFF MECHANISM FOR BAG USED FOR CONDITIONING, RECONSTITUTING AND/OR DILUTING OF INJECTABLE PRODUCTS

CROSS-REFERENCE TO RELATED APPLICATIONS

This application claims benefit of PCT/BR2017/050183 filed Jul. 6, 2017, which claims benefit of Brazilian Patent Application Serial No. 10 2016 016091 0 filed Jul. 11, 2016, both of which are incorporated by reference in their entirety.

BACKGROUND OF THE INVENTION

1. Technical Field

Human or animal health sector.

2. Related Art

Products intended for parenteral (injectable) delivery are provided to the consumer market in their final usage form (liquid products) or in a previous phase, such as powders (injection powders) that require addition of diluent in order to reconstitute the injectable product.

The best example on the state of the art is the preparation of said powder for injectable use.

Accessing the powder inside the bottle for addition of the diluents is done by piercing the stopper using a metallic needle. As soon as the product is reconstituted, in case dilution inside a bag is required, transfer to said bag is done by piercing the bag membrane with a metallic needle.

For infusion of said diluted product, another bag membrane is pierced using equipment with a spike (plastic needle).

Piercing the bottle's stopper and the bag membrane using a metallic needle or a spike (plastic needle) are processes that potentially generate particles, as well as unsafe, due to the likelihood of puncturing accidents and contaminations.

Our input for avoiding particles and reducing puncturing accidents and contaminations has led to the filing of a patent application on Sep. 29, 2010, PI 1003460-9, with a Letter Patent issued on Jan. 6, 2015.

Said patent integrates several improvements, eliminating the inconveniences verified in the state of the art of the bags currently in the market.

The bag proposed in patent 1003460-9 innovated in proposing entry and exit points equipped with open-close mechanisms, warning about the use of a particle retaining filter regarding the need for attachment of a bottle to a spike (plastic needle) at the entry point, as well as integrating a luer-lock termination (luer-lock is the universal designation of a thread type used in medical and pharmaceutical devices) at the exit point for access with a luer-lock syringe or luer-lock infusion equipment, without need or a needle or spike.

Therefore, the possibility of introducing particles released by membrane perforation to the bag was fully eliminated immediately, since said membranes were removed from the bag proposed in our patent application PI 1003460-9.

In the patent application PI 1003460-9, considering the exit point equipped with an open-close mechanism and luer-lock terminal, we hereby attest the possibility to manufacture the bag solely with said exit point, thus transformed into a functional single-entry bag with no pierceable membranes, accessed only through a luer-lock syringe (no metallic needle), or an equally luer-lock infusion equipment (no plastic spike). This is the so called "No Coring Bag" (a bag that does not generate particles; "coring" means particle release caused by puncturing).

Upon granting of the patent, our industrial prototypes have caused an impression on professionals during our demonstrations. We were thrilled with the response and decided to permanently focus on the aforementioned functional single-entry bag, in anticipation that its usage might expedite preparation and delivery processes for injectable products, as well as provide safety to dosage fractionation, since all said phases would be carried out with no metallic needles or spikes (plastic needles).

Therefore, we have decided that a better open-close mechanism, as described on patent PI 1003460-9, is needed in order to provide operations that demand various opening and closure cycles of the system, such as, for example, dosage fractionation on injectable product preparation pharmacies.

Since it is a bag with no membranes, which allows use of luer-lock syringes without metallic needles, and infusion equipment with luer-lock terminal and without spikes, said bag is also suitable for use in emergency situations, for example, inside ambulances, in disaster areas or conflict regions.

The preparation of injectable products, in particular, powders for injection, is carried out by piercing the stopper of the bottle that contains the product with a metallic needle, in order to add the liquid that will reconstitute the product, since said product may only be delivered in liquid form by parenteral (injectable) route.

As soon as the product is reconstituted, in case dilution inside a bag is required, transfer to said bag is done by piercing the bag membrane with a metallic needle, at said entry point. For infusion of said diluted product, another bag membrane is pierced using infusion equipment with a spike (plastic needle), at said exit point.

Some dilution bags are also provided with spikes (plastic needles) at the previously named entry point, so that the bottle is attached to said entry point; here also through transfixation of the stopper by said spike (plastic needle). The exit point of the bags also includes a membrane to be pierced by infusion equipment with a spike (plastic needle).

In summary, this is how nearly every powder for injection currently in the market is reconstituted (liquefied) and diluted (when concentration is reduced by adding more diluent).

Piercing the stopper of a bottle containing a product to be injected and, similarly, the membrane of the bag containing a diluents, using a metallic needle or a spike (plastic needle), are procedures considered unsafe due to the possibility of generating particles which, if not detected, may cause embolism on patients, and also unsafe due to the possibility of puncturing accidents and contaminations.

These are the issues faced every day at injectable product preparation units, regardless if said products are intended either for human or animal use.

Also, considering that injectable products are not always prepared at units especially designed for such purpose, and not always by individuals who received proper training and supervision, the likelihood of accidents and contaminations is greatly increased.

SUMMARY

This invention, named "WITH ON-OFF MECHANISM FOR BAG USED FOR CONDITIONING, RECONSTI- TUTING AND/OR DILUTING OF INJECTABLE PRODUCTS", is a response to problems arising out of the state of the art as mentioned in the previous item.

This valve is a device for opening and closing access to a bag that includes a single functional access point (which functions as an entry or exit point), and which may be submitted to countless opening and closing cycles.

This open-close device will be simply called valve, and it should be highlighted that it does not include membranes or stoppers to be pierced. Therefore, in order to access the contents of a bag including said valve, no metallic needles or spikes (plastic needle) are used, with any particle generation, puncturing accidents are eliminated, as well as substantially reducing contamination possibilities, as described below.

The "VALVE WITH ON-OFF MECHANISM FOR BAG USED FOR CONDITIONING, RECONSTITUTING AND/OR DILUTING OF INJECTABLE PRODUCTS" object of the present invention patent application, comprises five elements: a tapered tubular plastic base that is attached to the small plastic access tube of the bag; a mobile tapered plastic part that ends in a luer-lock shape; two rubber sealing O-rings; a plastic cover which, in addition to protecting the luer-lock terminal, prevents the detachment of the mobile part from the valve.

The present patent provides that the opening and closure valve includes a luer-lock terminal protected by a cover which will be open only during use.

When the valve is closed, even though a luer-lock syringe or equally luer-lock type infusion equipment is attached to said valve, it will only open with a traction motion, while holding the syringe barrel or the infusion equipment chamber; when open, the opposite motion closes the valve.

Therefore, such bag model may be used to prepare a product in a clean area and to attach a syringe or infusion equipment to the valve, with no need to open the system; the valve will be opened by the traction motion only when the contents of the bag are to be actually used.

BRIEF DESCRIPTION OF THE DRAWINGS

The "VALVE WITH ON-OFF MECHANISM FOR BAG USED FOR CONDITIONING. RECONSTITUTING AND/OR DILUTING OF INJECTABLE PRODUCTS", object is the present invention patent application, is described in detail by the figures below.

DETAILED DESCRIPTION OF THE PREFERRED EMBODIMENTS

The "VALVE WITH ON-OFF MECHANISM FOR BAG USED FOR CONDITIONING. RECONSTITUTING AND/OR DILUTING OF INJECTABLE PRODUCTS", object of the present invention patent application, hereinafter simply referred to as valve, comprises: two tapered plastic parts attachable to each other; two rubber sealing O-rings, one of said rings having a larger diameter which, in addition to helping with side sealing, provides easier sliding between the parts, and a smaller diameter ring which seals the lower section of the valve, preventing liquid flow when the valve is closed; a plastic cover that protects the luer-lock terminal of the mobile tapered part and also prevents detachment of the mobile tapered part from the valve. All materials used in the structure of the valve are suitable for medical and pharmaceutical applications.

Figure 19:
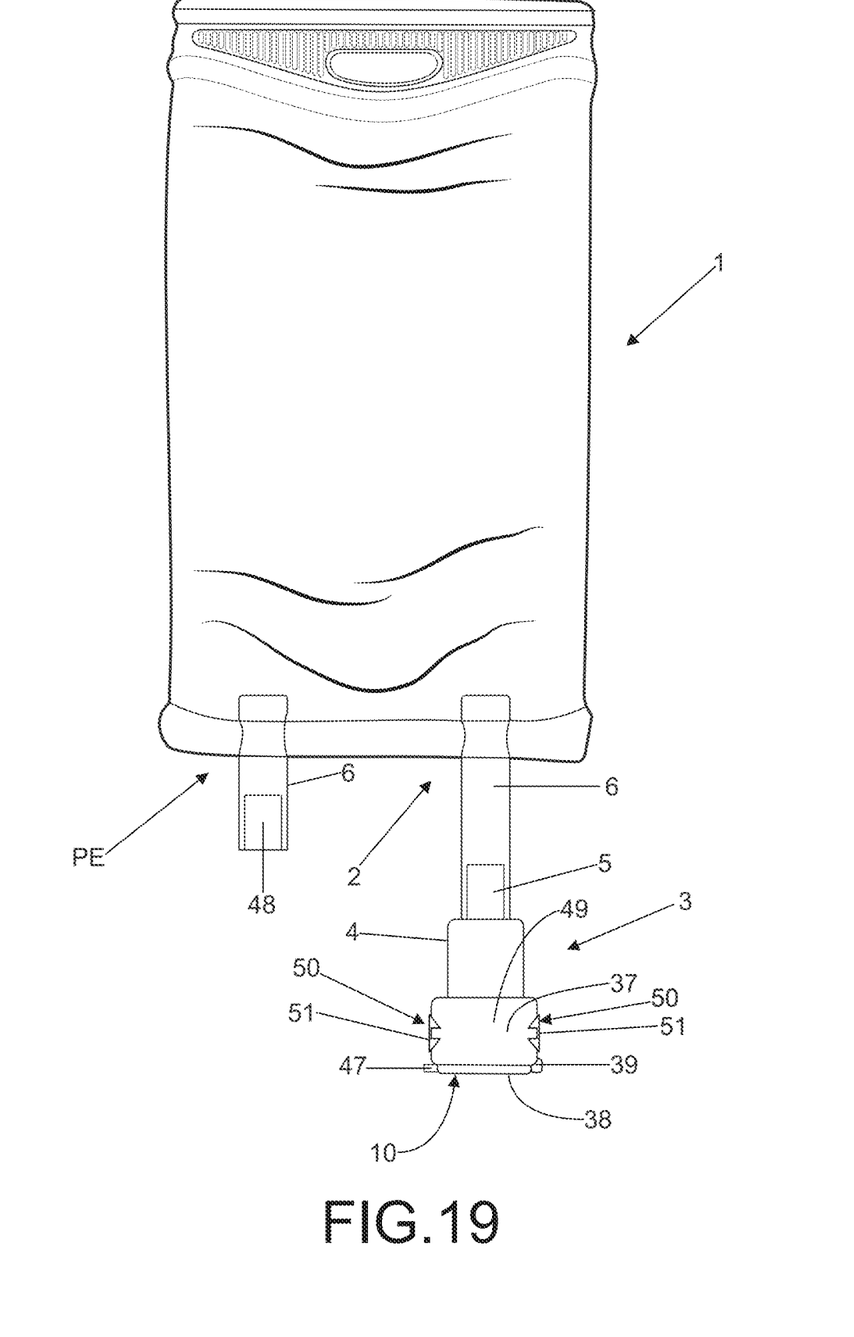
FIG. 19 shows the valve already attached to the bag.

Below are featured the details of the valve, object of this patent application, in reference to the aforementioned figures:

FIG. 19: Valve 3 must be attached to the small access tube 6 of the bag 1 which ends up with a single functional access point 2. This access point functions as an entry or exit point. Valve 3 includes a tapered base 4 which is narrowed, defining a 5 to connect with the small access tube 6 of the bag 1. The tubular terminal 5 features the inner channel 35 that ends in an opening 36.

Figure 6:
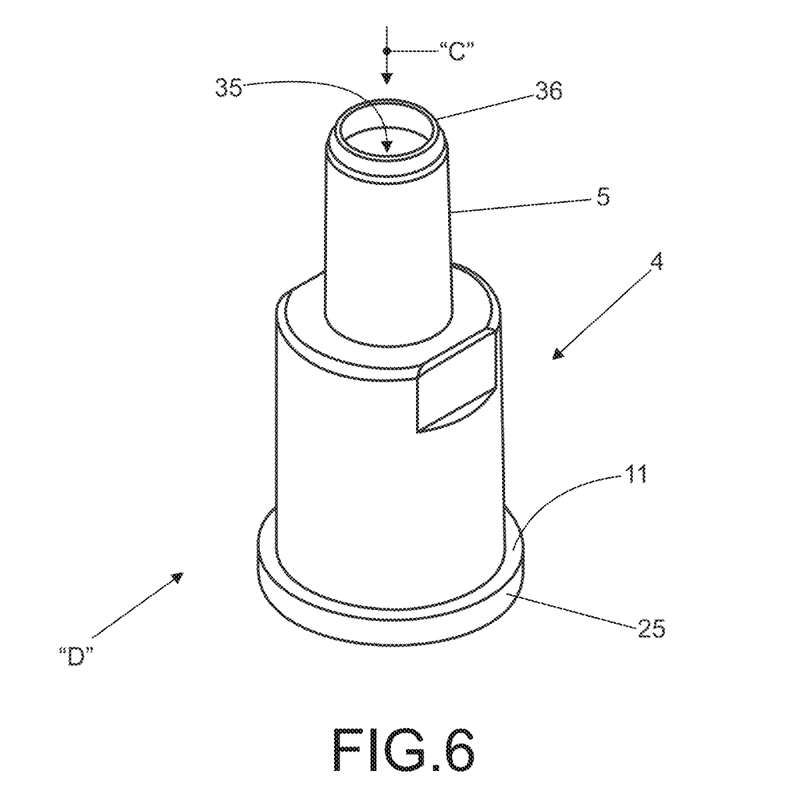
FIG. 6 shows a view from the tapered base of the valve which will be coupled to the small access tube of the bag.
Figure 7:
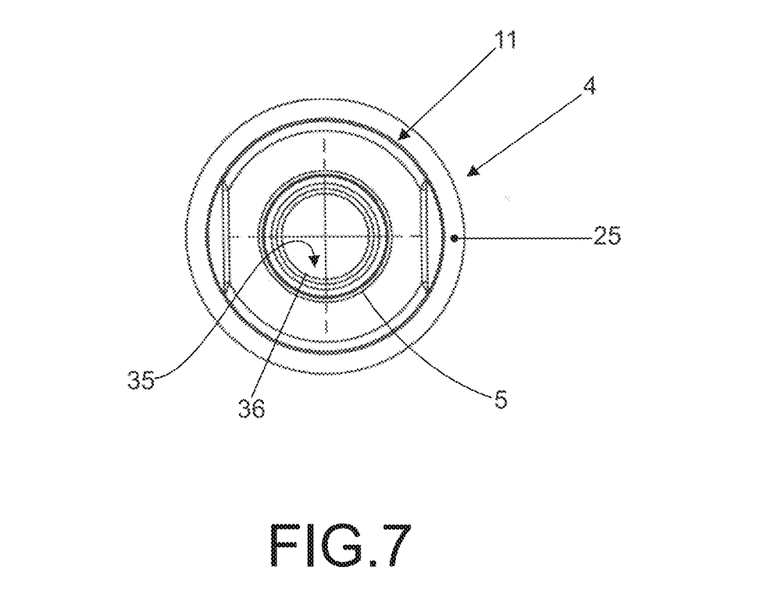
FIG. 7 shows a view indicated by arrow "C" of FIG. 6.
Figure 8:
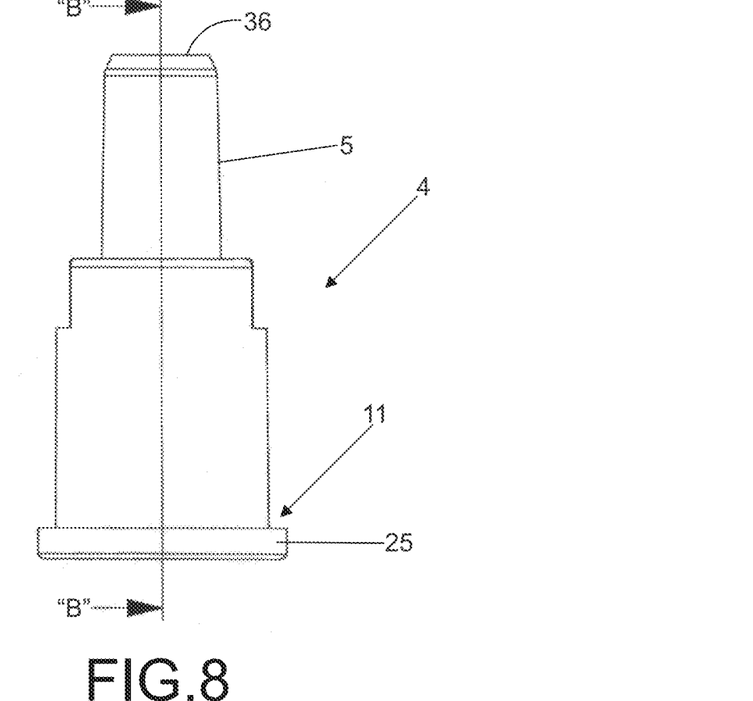
FIG. 8 shows a view indicated by arrow "D" of FIG. 6.
Figure 10:
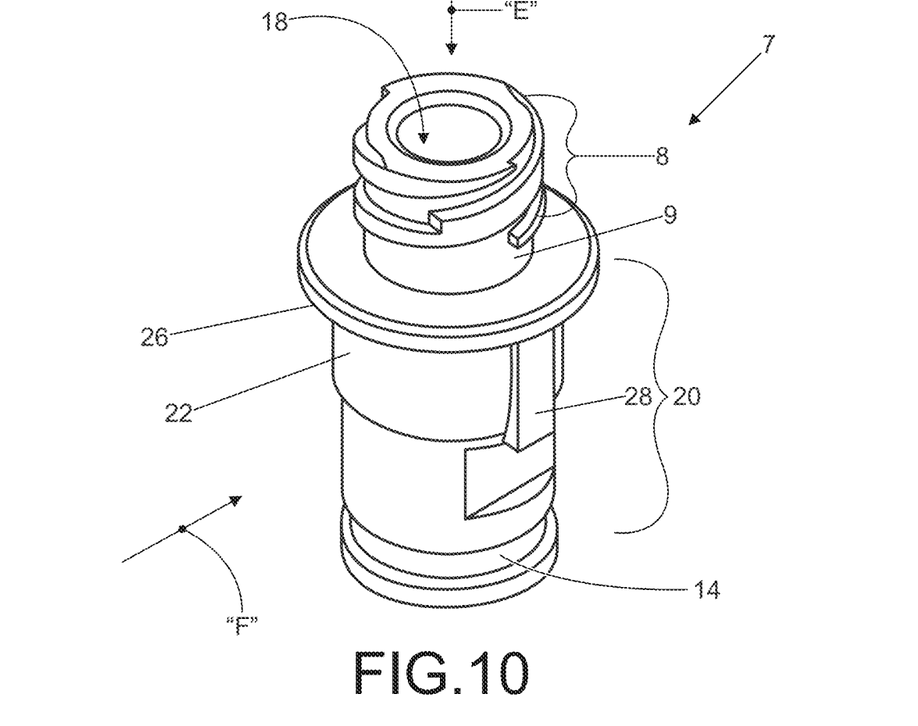
FIG. 10 shows a view from a mobile tapered part with its luer-lock terminal.
Figure 11:
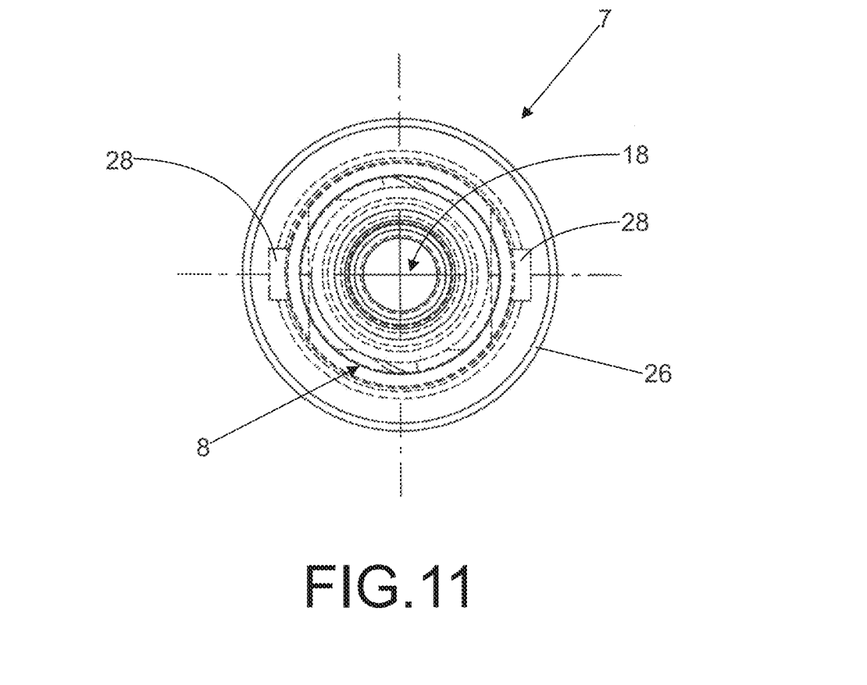
FIG. 11 shows a view indicated by arrow "E" of FIG. 10.
Figure 12:
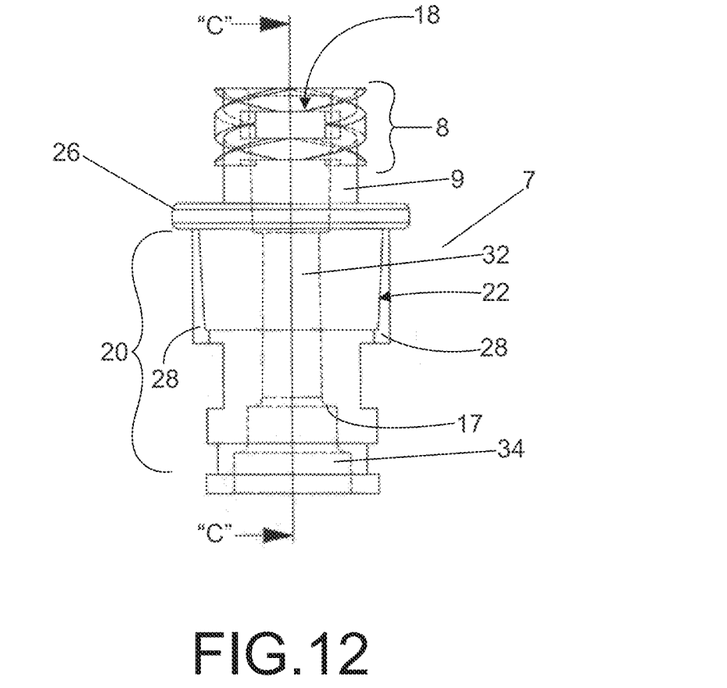
FIG. 12 shows a view indicated by arrow "F" of FIG. 10.
Figure 13:
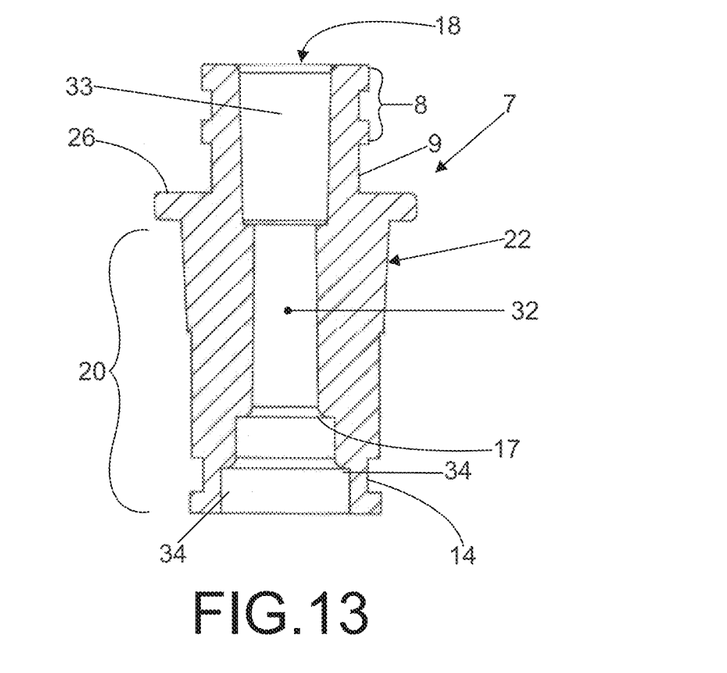
FIG. 13 shows a view outlined by the cut line "C"-"C" of FIG. 12.
Figure 14:
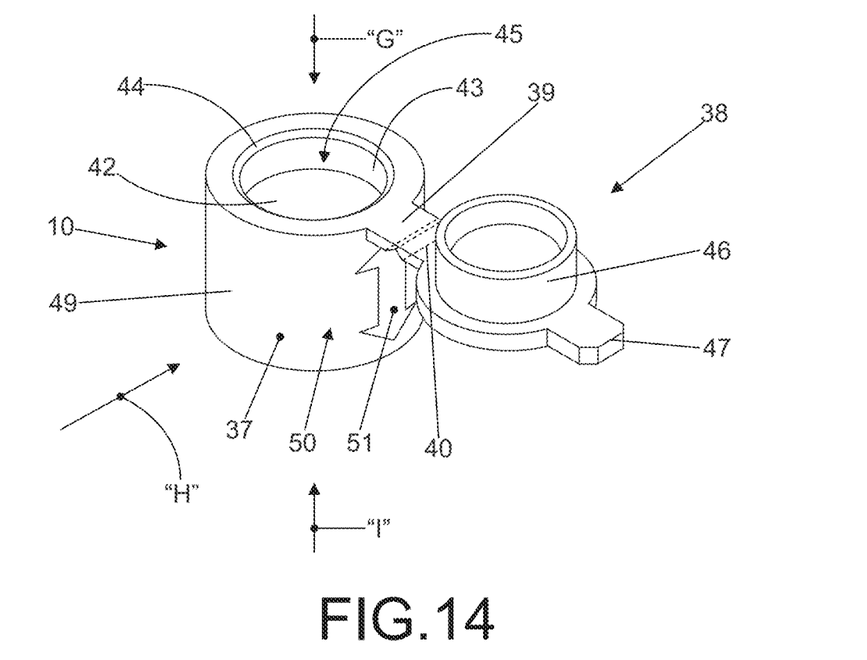
FIG. 14 shows a view of the cover that protects the luer-lock terminal and also prevents that the mobile part gets detached from the valve.
Figure 15:
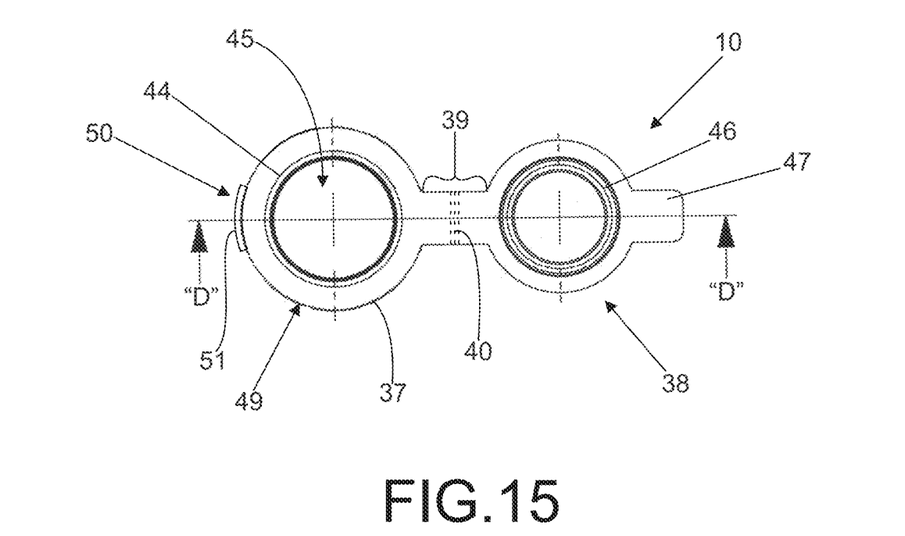
FIG. 15 shows a view indicated by arrow "G" of FIG. 14.
Figures 16, 17:
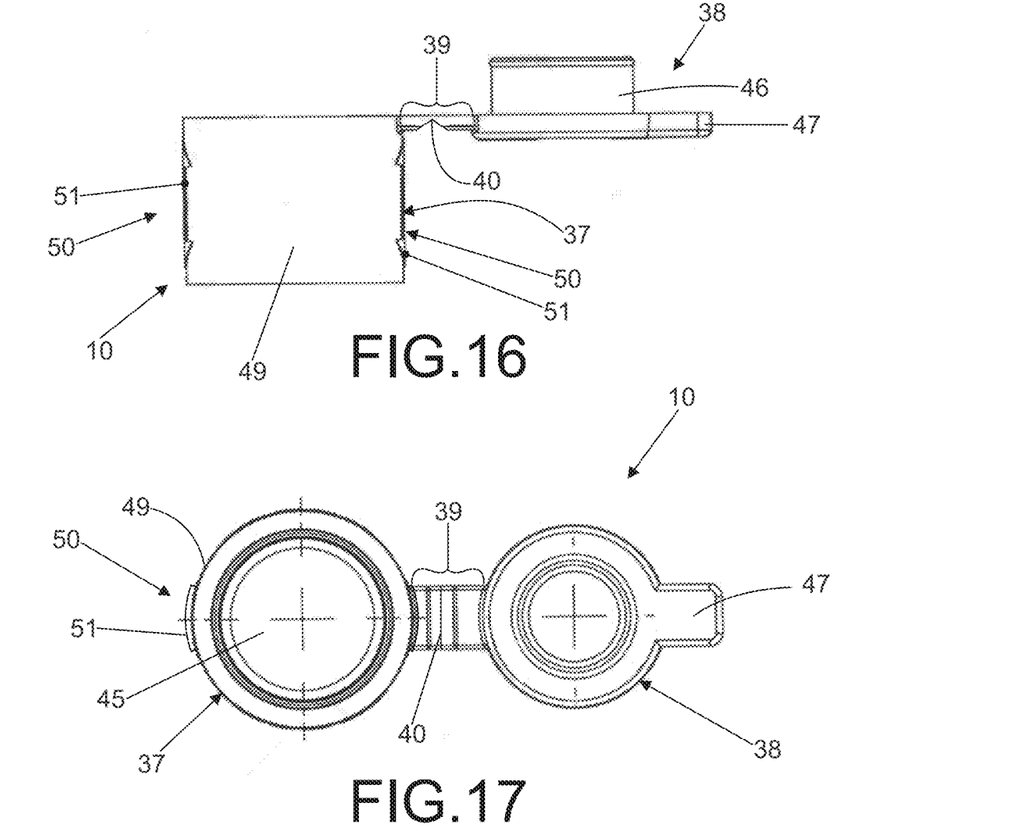
FIG. 16 shows a view indicated by arrow "H" of FIG. 14.
FIG. 17 shows a view indicated by arrow "I" of FIG. 14.

FIG. 6: A mobile tapered part 7 is inserted in the tapered base 4 (as seen in FIG. 10), with terminal 9 including a luer-lock type thread 8.

Figure 1:
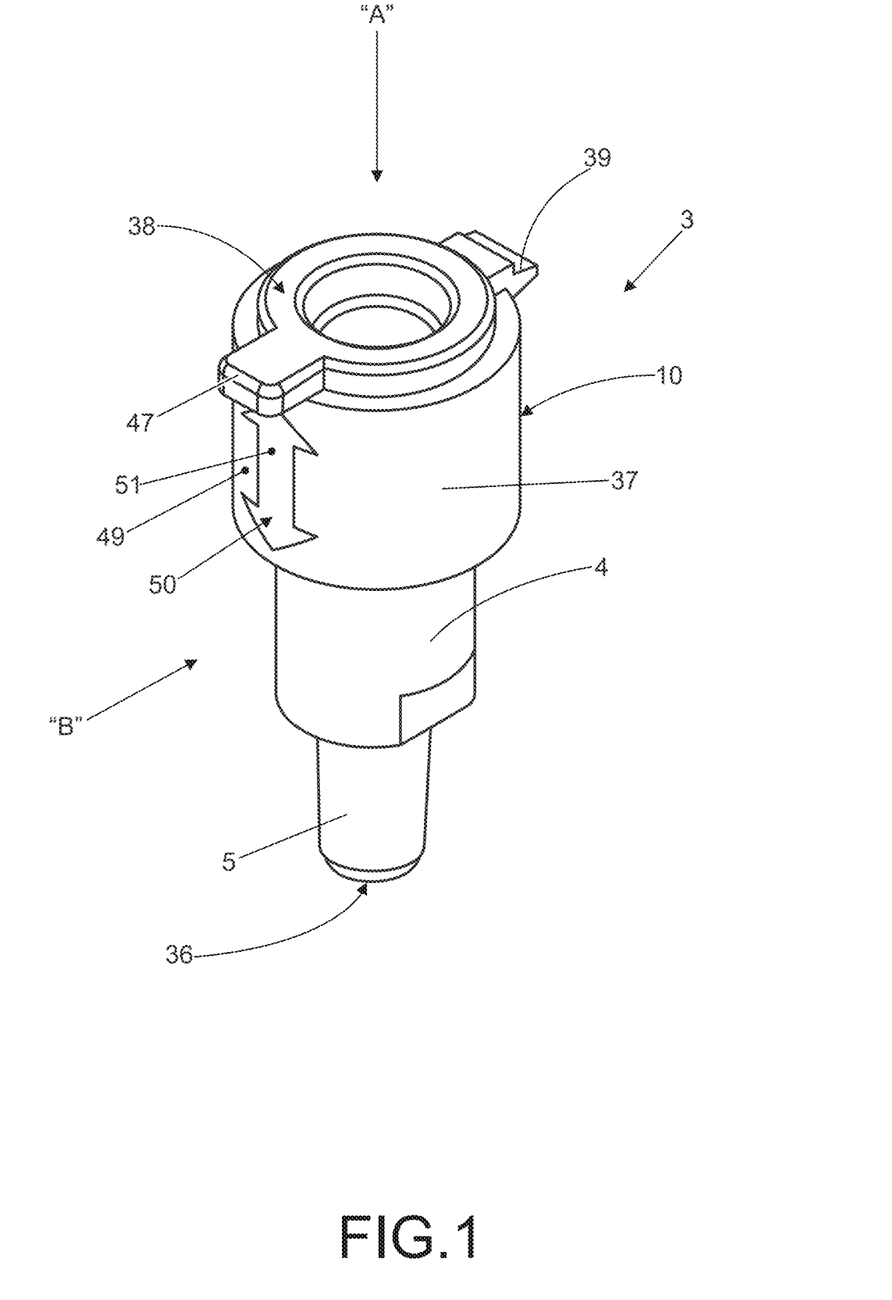
FIG. 1 shows a perspective view of the valve, prior to attachment to the bag.
Figure 2:
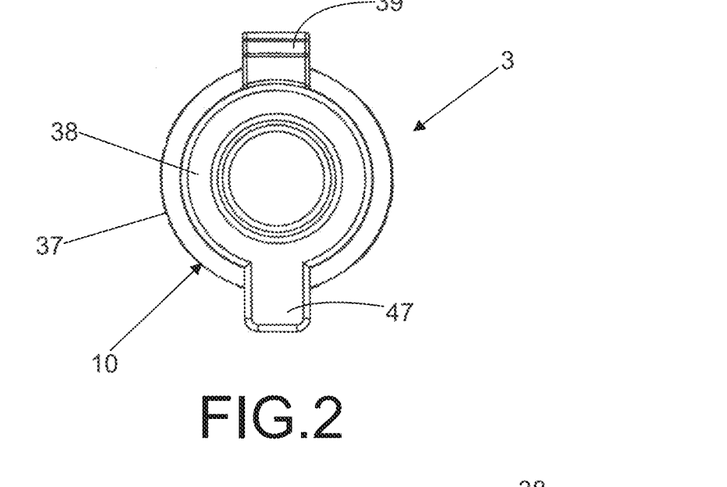
FIG. 2 shows a view indicated by arrow "A" of FIG. 1.
Figure 3:
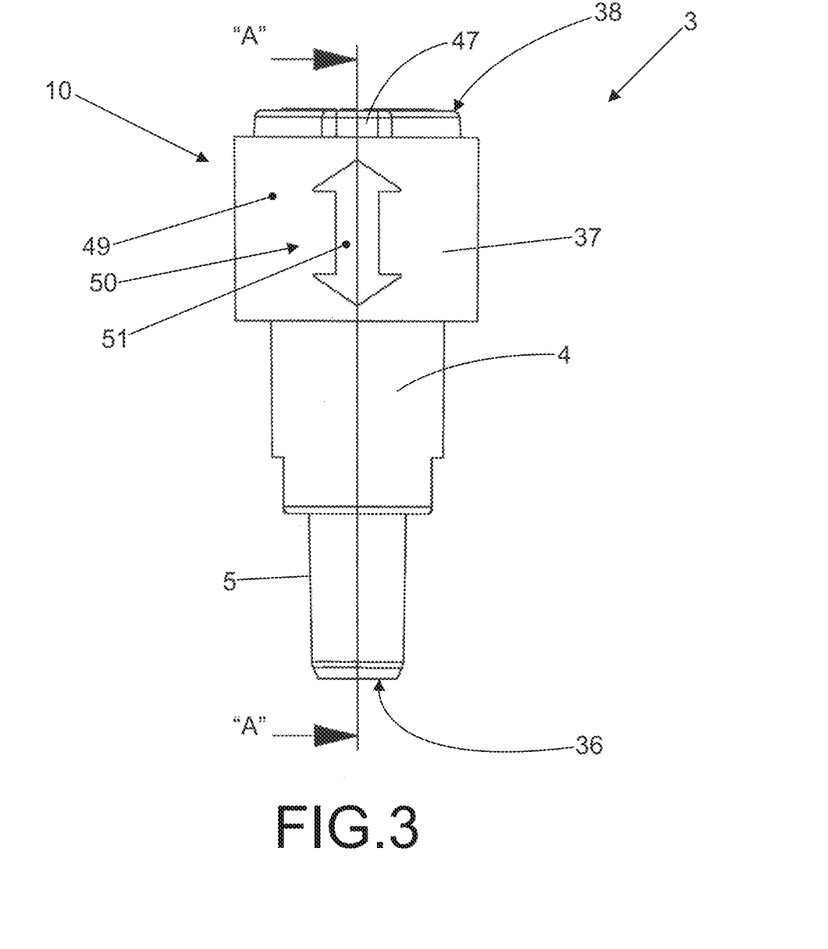
FIG. 3 shows a view indicated by arrow "B" of FIG. 1.
Figure 4:
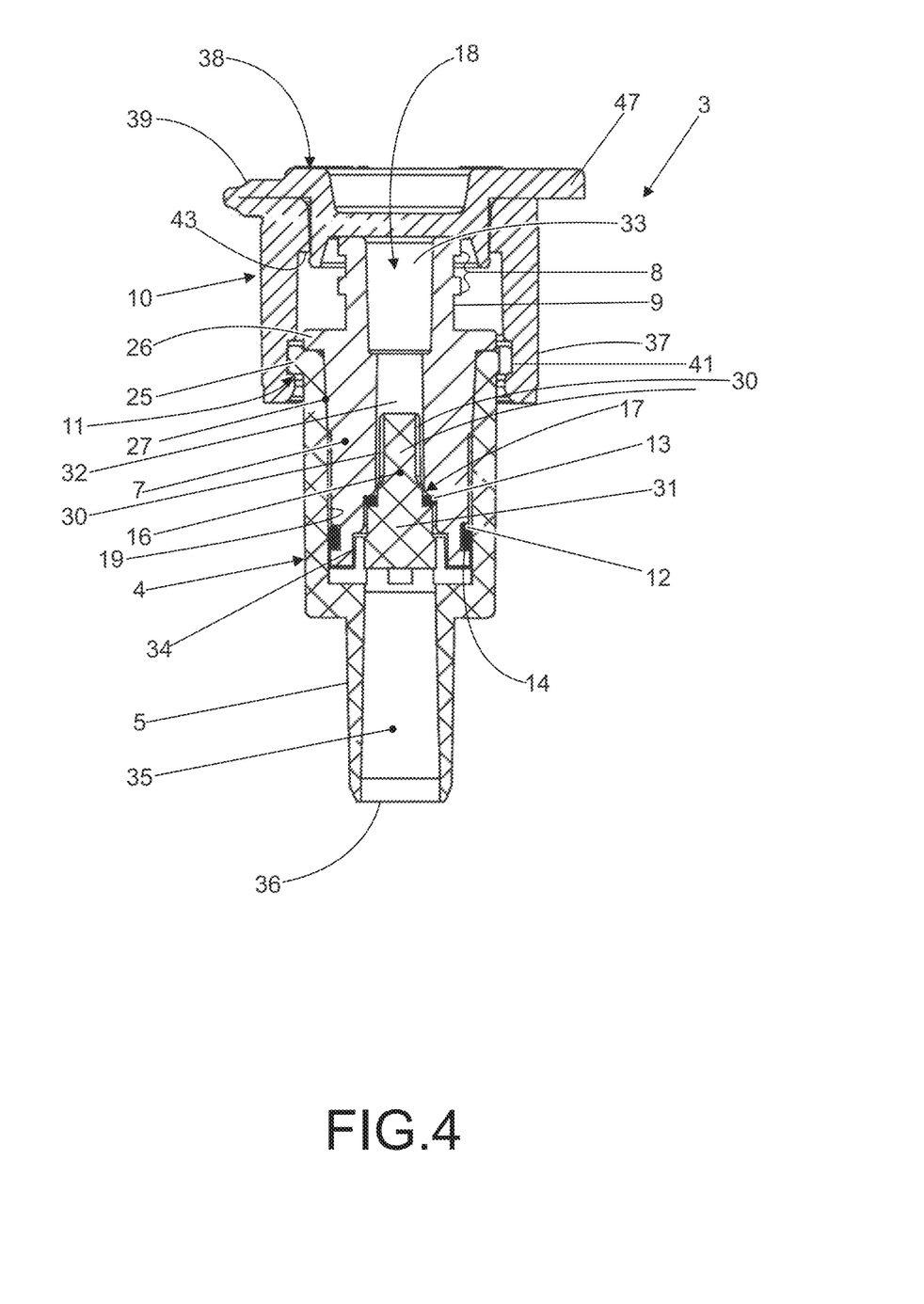
FIG. 4 shows a view outlined by the cut line "A"-"A" of FIG. 3.

FIG. 4: A cover 10 is modeled to the end part 11 of the tapered base 4 to protect the luer-lock terminal of the mobile tapered part 7 and also prevent detachment of said part from the valve 3.

Valve 3 includes two sealing O-rings: a larger diameter ring 12 is mounted to the lower groove 14 of the mobile tapered part 7; said sealing ring 12, in addition to sealing, provides easier sliding of the mobile tapered part 7. A smaller diameter sealing O-ring 13 is mounted to the lower part of the core 16 of the tapered base 4; said sealing ring 13 provides sealing of the lower surface and prevents liquid from flowing out of the bag when the valve 3 is closed. When valve 3 is fully closed, the sealing ring 13 remains in contact with the diameter reduction region 17 that constitutes the axial channel 18 of the tapered part 7.

Figure 5:
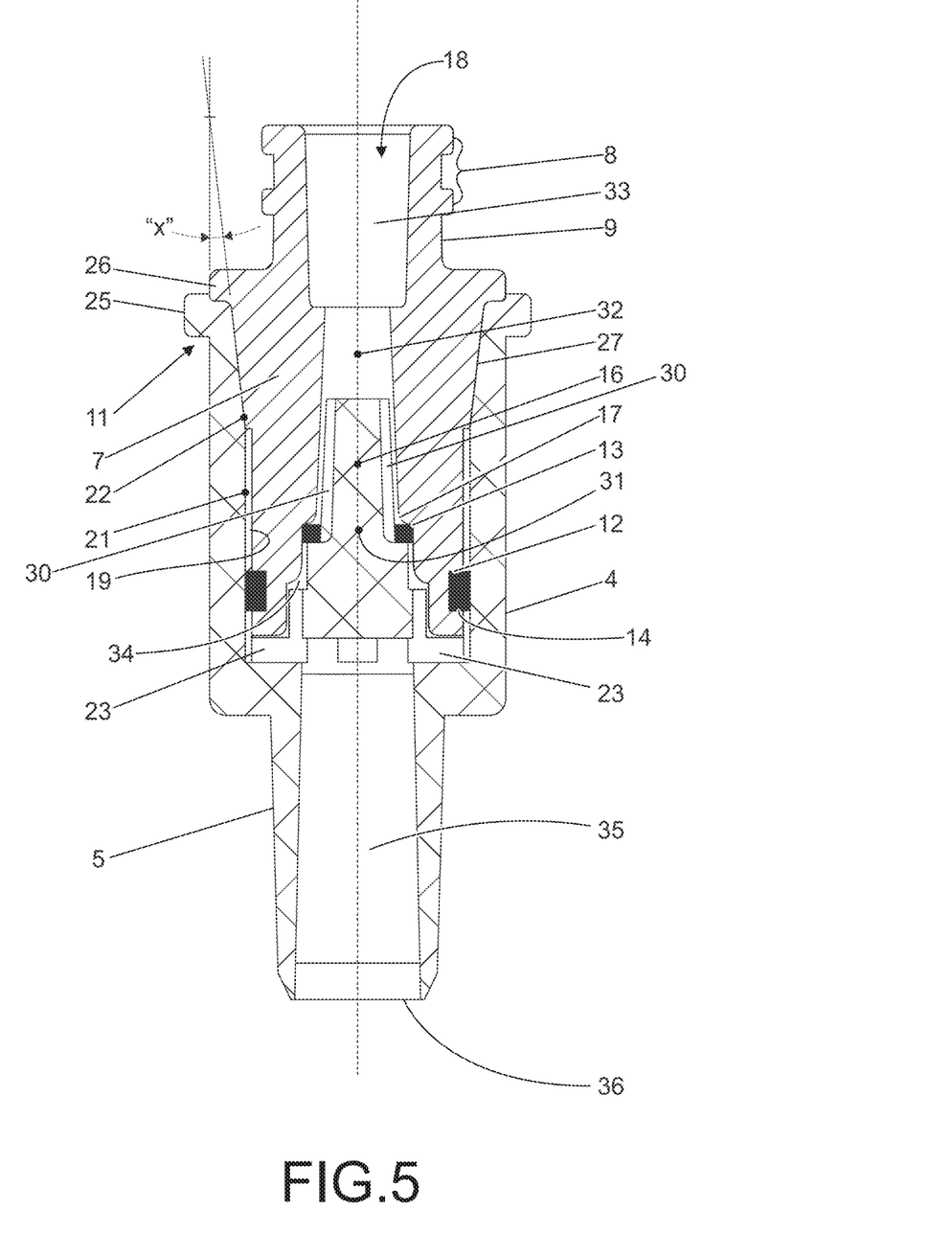
FIG. 5 shows an expanded detail of the components that enable the open-close motion of the valve in its fully closed position.

FIG. 5: The mobile tapered part 7, as the name implies, is slightly tapered as demonstrated by its surface 22 which contacts the inner surface 27 of the tapered base 4; "x" indicates the slight angle between the tapered parts; the core 16 of the tapered base 4 features bas-relief grooves 30 extended along the respective section 31, which is fully inserted in the median portion 32 of the axial channel 18, which comprises an initial portion 33, the aforementioned median portion 32 and a larger diameter portion 34. The tapered base 4 includes the housing 19 which receives the main portion 20 (as seen in FIG. 10) of the mobile part 7. The mobile part 7 features a ring edge 26 which is in contact with the ring edge 25 of the tapered base 4, whenever the valve 3 is closed.

Figure 5A:
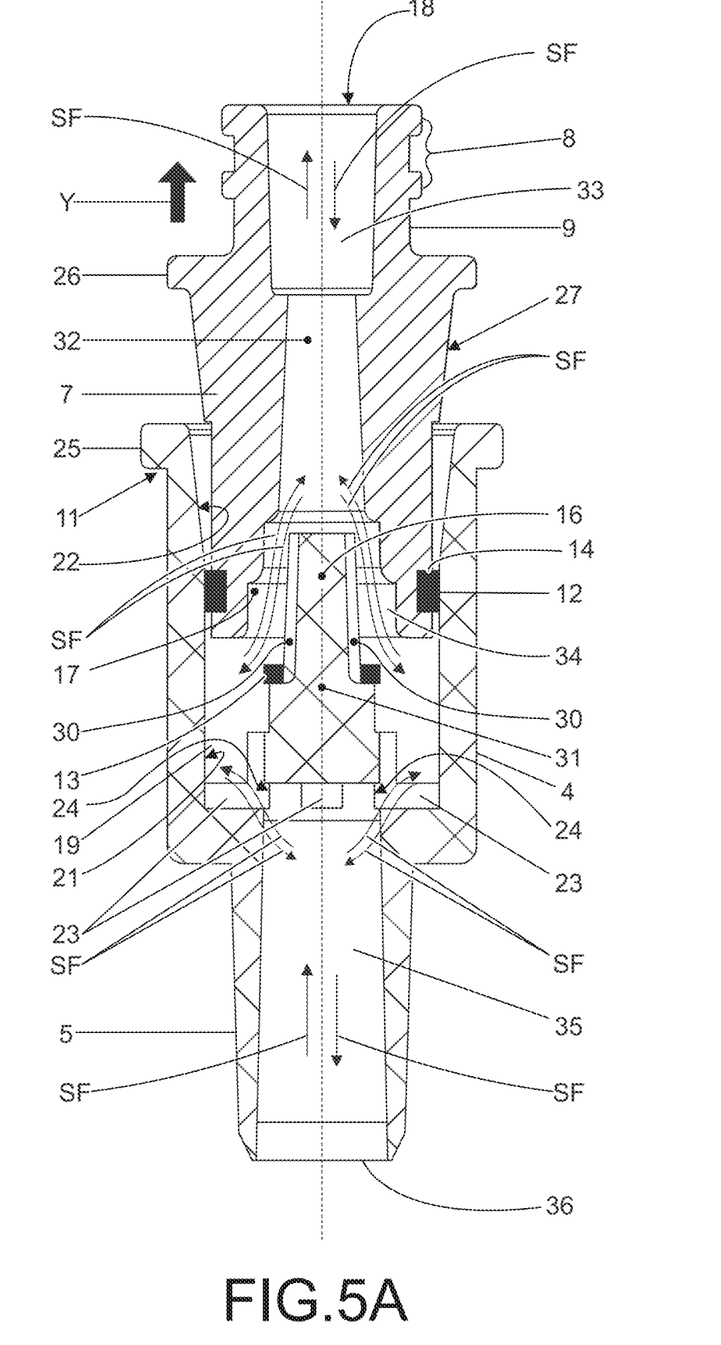
FIG. 5A shows an expanded detail of the components that enable the open-close motion of the valve in its fully opened position.

FIG. 5A: There are four small liquid flow channels 24 at the lower part of the tapered base 4; the liquid flow through the valve 3 is indicated by the flow arrows SF. The liquid flow channels 24 are formed between radial walls 23 that connect the core 16 to the inner structure of the tapered base 4.

Movement between both tapered parts of the valve 3 takes place without side liquid leakage, due to the conicity and the larger diameter sealing ring 12, which maintains permanent contact with the housing 19 wall of the 4 and the mobile tapered part 7. The arrow Y indicates the relative movement between the mobile tapered part 7 and the tapered base 4.

Figure 9:
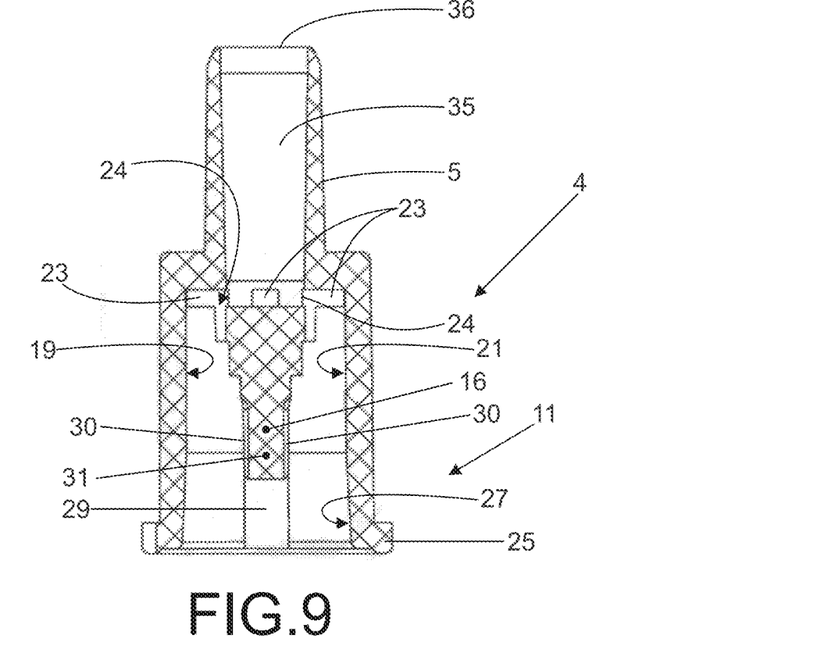
FIG. 9 shows a view outlined by the cut line "B"-"B" of FIG. 8.

FIG. 9: The lower part 11 of the tapered base 4 includes a ring edge 25 which is an attachment point for the cover 10 that protects the valve 3, as seen below. There are two attachment grooves 29 (one is seen herein) explained below.

FIG. 10: The mobile tapered part 7 includes two radially opposite protrusions 28 (only one of them is seen in this figure) which are coupled to both grooves 29 mentioned in the description of FIG. 9. Said couplings prevent the rotation between the parts 4 and 7 when a luer-lock syringe S or luer-lock infusion equipment (EI) is attached or detached from the valve 3.

Figure 18:
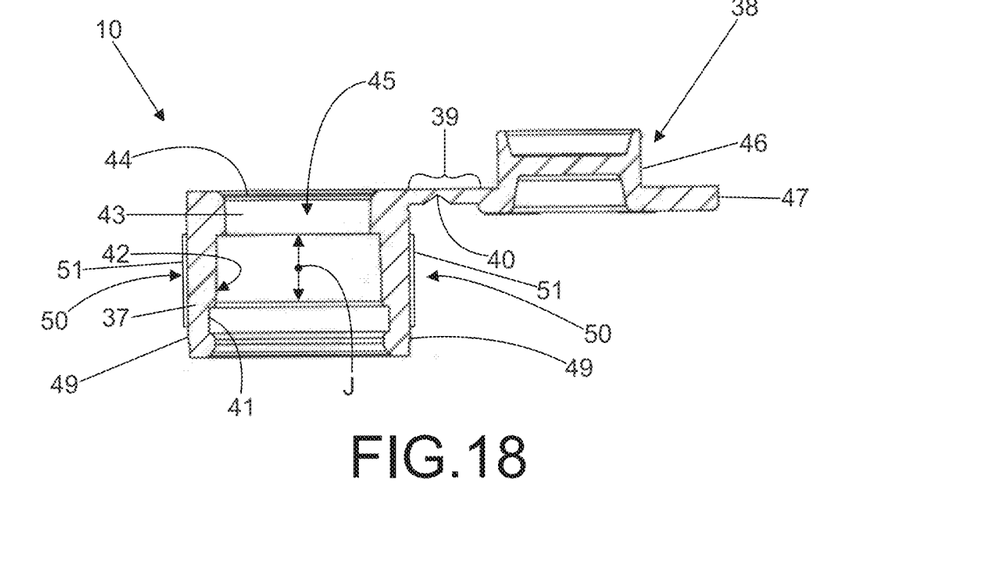
FIG. 18 shows a view outlined by the cut line "D"-"D" of FIG. 15.

FIG. 18: The plastic cover 10 includes a tube portion 37 which has, in its inner surface, a ring groove 41 in which the ring edge 25 is attached to the tapered base 4, in order to fasten the plastic cover 10 to the tapered base 4; the tube portion 37 also features, in its inner surface, a reduction in diameter 43 which delimitates the motion extension of the mobile tapered part 7 and prevents disconnection from the valve 3. Said motion extension, adjusted in order to enable valve opening or closure of the valve, is illustrated by arrow J.

The plastic cover 10 includes a flap with a deep V-shaped crease 40 which transforms it into a foldable flap 39; said foldable flap 39 is placed between the tube portion 37 and the cover portion 38; the inner tube wall 42 of the plastic cover 10, on its upper part, has a reduction in diameter 43, delimiting a circular opening 45 which, in turn, is delimited by a tapered truncated edge 44, to which the plastic protrusion 46 is pressure attached, ensuring full sealing of the cover 10. The cover 10 is opened or closed using its radial flap 47 as a grip point.

The double arrow 51, inserted as an embossed area 50 on the wall 49, guides opening (downward indication) and closure (upward indication) motions of the valve 3.

Figure 20:
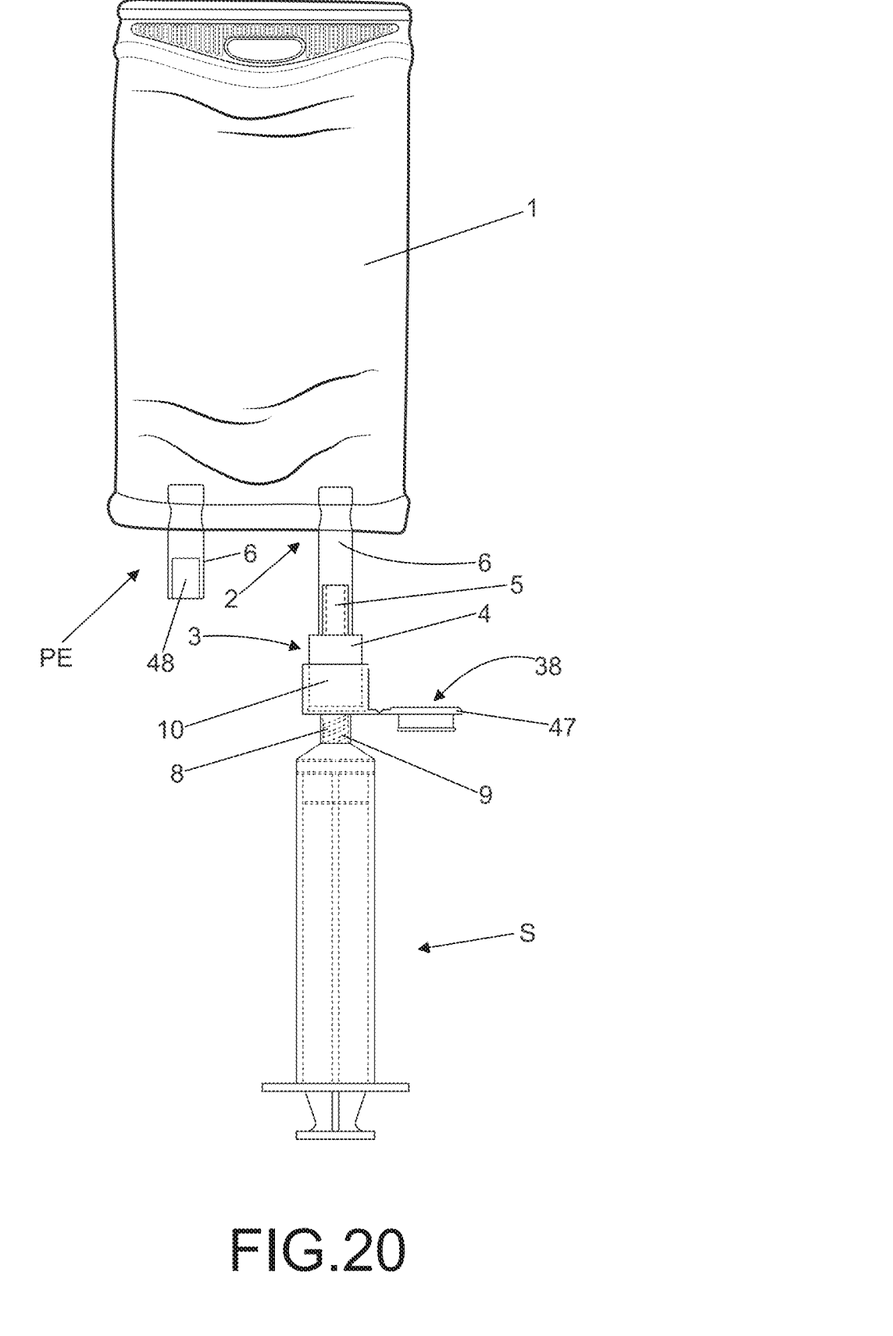
FIG. 20 shows a syringe with a luer-lock terminal attached to the valve.

FIG. 20: When the cover 10 is opened, a syringe S (see FIG. 21 in which the metallic needle is removed), with a luer-lock terminal, may be attached to terminal 9 including a luer-lock thread 8 of the valve 3, through a clockwise rotating movement; driving the syringe S opens the valve 3; opposite movement closes the valve and detaches the syringe. It is, therefore, through syringe S (without the needle) directly coupled to valve 3 by the luer-lock terminal 8-9 that the contents of the bag 1 are accessed.

Figure 21:
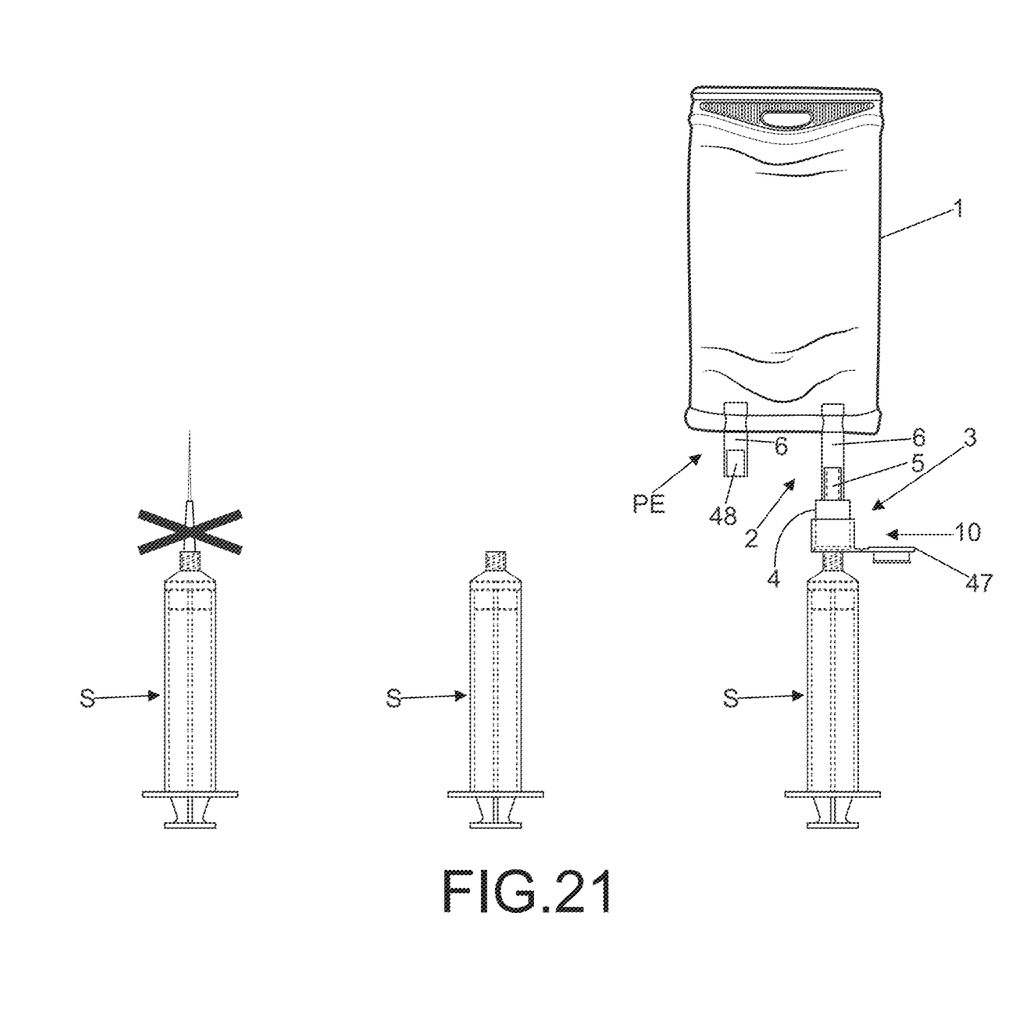
FIG. 21 shows a syringe with needle (indicating the needle is removed afterwards); a syringe with a luer-lock terminal to access the valve; the syringe itself, with a luer-lock terminal, attached to the valve.

FIG. 21: A syringe S with a metallic needle (indicating the needle will be removed) is also shown; syringe S with a luer-lock terminal 8-9 to be attached t valve 3; the syringe attached to the valve 3.

Figure 22:
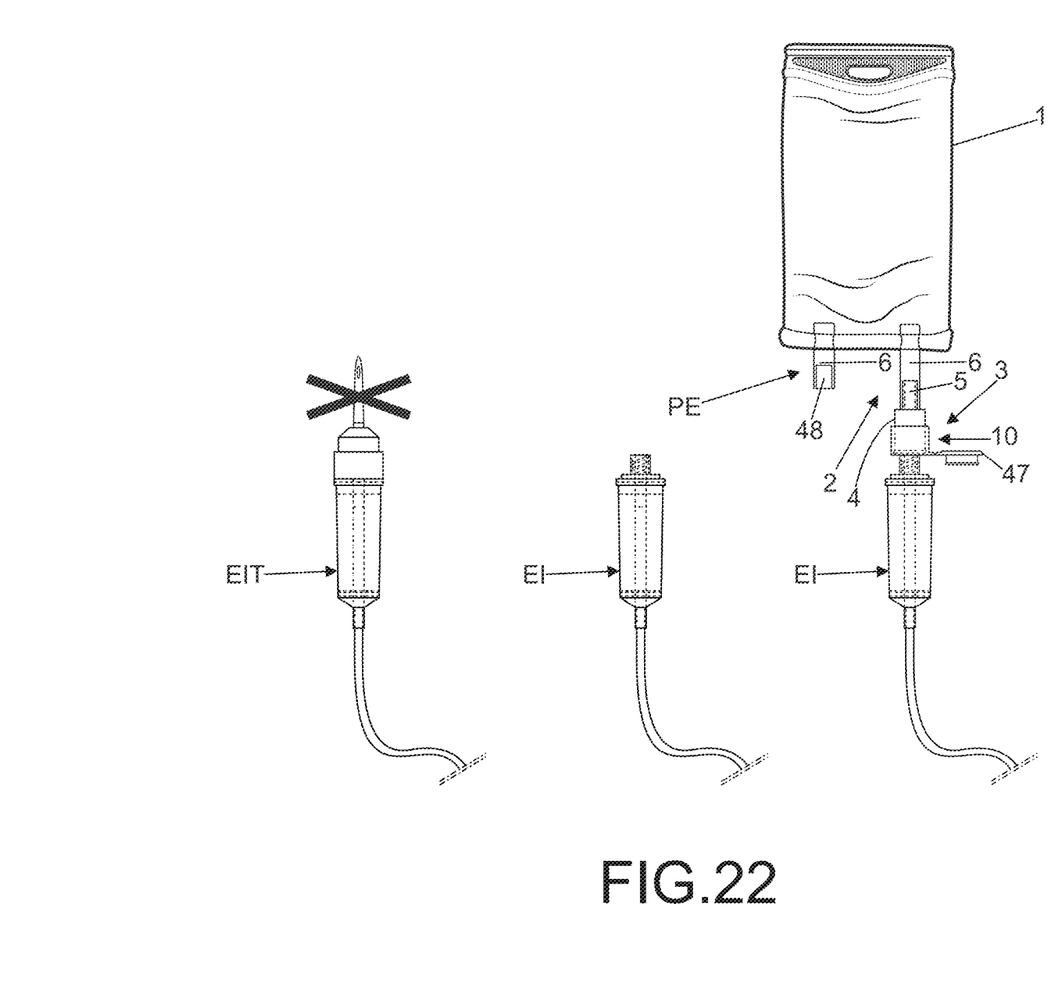
FIG. 22 shows a standard infusion equipment, including a spike (plastic needle) (indicating said spike is removed afterwards); an infusion equipment with a luer-lock terminal (especially designed for use with the valve, object of the present patent application); the infusion equipment with a luer-lock terminal attached to the valve.

FIG. 22: When the cover 10 is opened, an infusion equipment EI with a luer-lock terminal (equipment especially designed for use with the valve 3, object of this patent application), may be attached to terminal 9 with a luer-lock thread 8 of the valve 3 through a clockwise rotating movement; driving the equipment EI opens the valve 3; opposite movement closes valve 3e and disconnects the equipment EI.

FIG. 22: Further shows a standard infusion equipment (EIT), including a spike (plastic needle) (indicating said spike will be removed); the infusion equipment EI with a luer-lock terminal (equipment especially designed for use with the valve 3, object of the present patent application) to be attached to valve 3; the equipment EI with a luer-lock terminal attached to the valve 3.

The valve 3, arising out of the improvement of the mechanism described in our previous patent PI 1003460-9, has been submitted to comprehensive testing. Said valve may be submitted to sterilization by gamma radiation, ethylene oxide or hot steam; when closed, withstands compression up to 2 BAR, with no leaks (thus significantly beyond current specifications, which provide that bags are leak tested for compression of 0.5 BAR). Valve 3 was also submitted to countless opening and closure cycles, with no leaks, which attests safe usage in injectable product preparation stations and during intravenous infusions.

As it is mounted on a plastic bag, with no pierceable membranes, does not generate coring (particle release due to perforation), therefore being characterized as a proper "No Coring Bag" (no particle generation).

Another groundbreaking feature is that said valve provides full safety when handling the bag: access to the contents is done with a luer-lock syringe (no metallic needle) and/or infusion equipment without spike (plastic needle), needles and spikes usually cause puncturing accidents, as well as increasing the likelihood of contamination. One must only observe a daily hospital routine in order to understand the puncturing accident and contamination hazards when, for example, equipment with spike is detached from a bag and must be re-attached to another bag, a situation that takes place hundreds of times in any hospital, every day. These unsafe procedures are rectified by our valve 3. With said valve 3, universal use of the infusion equipment with luer-lock terminal EI (equipment especially designed for use with the valve 3, object of said patent application) is now possible, which will be provided, also in an innovative character, with the new bag featuring our valve 3.

With the inclusion of rings 12 and 13 and measurement adaptations between components, since said valve was fully upgraded in laboratory, the use of sealing systems was no longer required, as provided in our previous patent (PI 1003460-9), for the first opening of the valve, provided that the cover was also adjusted to ensure full sealing.

It should be highlighted that, although the bag 1 shown in FIGS. 19, 20, 21 and 22 shows a filling port PE, said port may or may not be provided, depending on the packaging technique used for the bag 1: for example, the bag 1 may be packaged and the valve 3 may be placed afterwards on the same port (in this case, the aforementioned filling port PE is not required); in addition, firstly the valve 3 may be molded to the bag 1 and packaging is done through said filling port PE, defined by a small access tube 6, which is to be permanently closed by a bung 48 after the packaging of the bag 1. Therefore, the bag 1 assembled with the valve 3, object of this patent application, will always be a functional single-entry bag (for addition or extraction of liquid through the same entry or exit point).

The invention claimed is:

1. A valve for integration with a bag having a single access point and used for conditioning, reconstituting, and/or diluting injectable products, the valve comprising:
    a tapered base having a channel defined by an inner surface at least part of which is disposed at an angle, the tapered base also having a core disposed inside the channel, the core having an outer portion;
    a mobile tapered part at least partially disposed inside the tapered base, wherein the mobile tapered part has an outer surface at least part of which is disposed at an angle, the angle of the outer surface of the mobile tapered part being the same as the angle of the inner surface of the tapered base, wherein the mobile tapered part also has a terminal end containing a luer-lock type thread;
    a first sealing O-ring disposed around the core of the tapered base to seal a space between the core and the mobile tapered part;
    a second sealing O-ring disposed around the mobile tapered part for sealing a space between the mobile tapered part and the tapered base and to facilitate sliding of the mobile tapered part in relation to the tapered base, the second sealing O-ring having a diameter that is larger than a diameter of the first; and
    a cover connected to the tapered base which protects the terminal end of the mobile tapered part and prevents detachment of the mobile tapered part from the tapered base.

2. The valve according to claim 1 where the tapered base further comprises a tubular terminal that connects to a small access tube of the single functional access point of the bag, the tubular terminal having an inner channel which terminates in an opening.

3. The valve according to claim 1 where the tapered base further comprises a ring edge to which the cover is attached; the ring edge being seated in a corresponding ring groove provided on the cover.

4. The valve according to claim 1 where the mobile tapered part further comprises a reduced diameter region that integrates an axial channel of the mobile tapered part, where the first diameter sealing O-ring remains in contact with the reduced diameter region when the valve is closed.

5. The valve according to claim 1 where the outer surface of the mobile tapered part is in contact with the inner surface of the tapered base when the valve is closed.

6. The valve according to claim 1 where the tapered base further comprises bas-relief grooves extending along the outer portion of its core.

7. The valve according to claim 4 where the axial channel of the mobile tapered part is defined by an initial portion, a median portion and a larger diameter portion.

8. The valve according to claim 1 where the channel of the tapered base receives a main portion of the mobile tapered part.

9. The valve according to claim 1 where the mobile tapered part further comprises a ring edge which contacts a ring edge on the tapered base whenever the valve is closed.

10. The valve according to claim 1 where the tapered base further comprises liquid flow channels which are defined by radial walls that connect the core to the inner surface of the tapered base.

11. The valve according to claim 1 where the outer surface of the mobile tapered part further comprises radially opposite protrusions which fit into grooves located in the channel of the tapered base.

12. The valve according to claim 1 where the cover further comprises a tube portion defined by an inner surface, the inner surface having a ring groove in which a ring edge on the tapered base is fitted for the purpose of fastening the cover to the tapered base, the inner surface of the tube portion having a reduced diameter region which delimits the motion extension of the mobile tapered part and prevents detachment from the valve.

13. The valve according to claim 1 where the cover further comprises a tube portion and a cover portion, the tube portion further comprising an inner surface and the cover portion further comprising a radial flap for gripping the cover portion, wherein the cover portion is connected to the tube portion via a foldable flap with a deep V-shaped crease, and wherein the inner surface of the tube portion has a reduced diameter region delimiting a circular opening which is further delimited by a tapered truncated edge to which a plastic protrusion on the cover is pressure attached, ensuring full sealing of the cover.

14. The valve according to claim 1 where a syringe with a luer-lock terminal is coupled to the valve by connecting the luer-lock terminal of the syringe to the luer-lock type thread on the terminal end of the mobile tapered part.

15. The valve according to claim 1 where an infusion equipment with a luer-lock terminal is coupled to the valve by connecting the luer-lock terminal of the infusion equipment to the luer-lock type thread on the terminal end of the mobile tapered part.

16. The valve according to claim 1 where the valve is opened or closed by sliding the tapered base in relation to the mobile tapered part, with the opening and closure of the valve being attained by the manual action of driving and pushing a syringe attached to it.

17. The valve according to claim 1 where the valve is opened or closed by sliding the tapered base in relation to the mobile tapered part, with the opening and closure of the valve being attained by the manual action of driving and pushing an infusion equipment attached to it.

18. The valve according to claim 1 where the cover further comprises an outer wall having an embossed area, wherein vertical movements determine the opening or closure of the valve, with the opening of the valve corresponding to downward movement and closure of the valve corresponding to upward movement.

19. The valve according to claim 14 where the syringe is coupled to the valve by rotating the syringe in a clockwise movement, and where the syringe is disconnected from the valve by rotating the syringe in a counter-clockwise movement.

20. The valve according to claim 15, where the infusion equipment is coupled to the valve by rotating the infusion equipment in a clockwise movement, and wherein the infusion equipment is disconnected from the valve by rotating the infusion equipment in a counter-clockwise movement.

* * * * *